US012564681B2

(12) United States Patent (10) Patent No.: US 12,564,681 B2
Menz et al. (45) Date of Patent: Mar. 3, 2026

(54) PEN-LIKE SYRINGE SYSTEM

(71) Applicant: Pharmpur GmbH, Königsbrunn (DE)

(72) Inventors: Dirk-Henning Menz, Diedorf (DE);
Klaus Ganser, Gilching (DE)

(73) Assignee: Pharmpur GmbH, Königsbrunn (DE)

( * ) Notice: Subject to any disclaimer, the term of this
patent is extended or adjusted under 35
U.S.C. 154(b) by 1032 days.

(21) Appl. No.: 17/635,146

(22) PCT Filed: Aug. 24, 2020

(86) PCT No.: PCT/EP2020/073645
§ 371 (c)(1),
(2) Date: Feb. 14, 2022

(87) PCT Pub. No.: WO2021/043614
PCT Pub. Date: Mar. 11, 2021

(65) Prior Publication Data
US 2022/0273876 A1 Sep. 1, 2022

(30) Foreign Application Priority Data
Sep. 5, 2019 (DE) ..................... 10 2019 123 870.6

(51) Int. Cl.
*A61M 5/20* (2006.01)
*A61M 5/168* (2006.01)
(Continued)

(52) U.S. Cl.
CPC ...... *A61M 5/2053* (2013.01); *A61M 5/16877*
(2013.01); *A61M 5/24* (2013.01);
(Continued)

(58) Field of Classification Search
CPC .............. A61M 5/2046; A61M 5/2053; A61M
5/16877; A61M 5/24; A61M 5/30;
(Continued)

(56) References Cited

U.S. PATENT DOCUMENTS

| 4,407,283 A | 10/1983 | Reynolds |
| 4,790,824 A | 12/1988 | Morrow |
| (Continued) | | |

FOREIGN PATENT DOCUMENTS

| CN | 101695593 A | 4/2010 |
| CN | 103230633 A | 8/2013 |
| (Continued) | | |

OTHER PUBLICATIONS

Second Office Action, dated Aug. 22, 2024, for Chinese Patent
Application No. 202080011207.2, 20 pages.
(Continued)

*Primary Examiner* — Lauren P Farrar
(74) *Attorney, Agent, or Firm* — Fleit Intellectual
Property Law; Paul D. Bianco

(57) ABSTRACT

A pen-like syringe system includes: a syringe holder for
receiving a syringe having a syringe barrel and a plunger
guided for movement in the barrel; and a drive housing
connected to the syringe holder. To provide an ergonomic
syringe system which allows advantageous operation of the
system and guarantees safe and focused injection or drawing
of a substance the drive housing includes an electric delivery
device operated by an integrated power supply for applying
pneumatic pressure or negative pressure to the plunger, with
the delivery device connected via a drive channel to the
plunger and actuatable by a button arranged on the syringe
system; and the pen-like syringe system has a vent duct with
a first end, which is connected to the drive channel, and a
second end, which is connected to the surroundings via an
opening, with the opening closable by pressing the button.

22 Claims, 5 Drawing Sheets

(51) Int. Cl.
| | |
|---|---|
| *A61M 5/24* | (2006.01) |
| *A61M 5/30* | (2006.01) |
| *A61M 5/31* | (2006.01) |

(52) U.S. Cl.
CPC ................ *A61M 5/30* (2013.01); *A61M 5/31* (2013.01); *A61M 2005/2026* (2013.01); *A61M 2005/2407* (2013.01); *A61M 2005/2496* (2013.01); *A61M 2005/3123* (2013.01); *A61M 2205/583* (2013.01); *A61M 2205/8237* (2013.01)

(58) Field of Classification Search
CPC .. A61M 2005/2026; A61M 2005/2407; A61M 2005/2496; A61M 2005/3123; A61M 2205/583; A61M 2205/8237; A61M 5/155; A61M 5/445; A61M 5/486; A61M 5/484; A61M 5/488; A61M 2005/3125; A61M 2005/31588; A61M 2205/8218; A61M 5/20

See application file for complete search history.

(56) References Cited

U.S. PATENT DOCUMENTS

| | | | | |
|---|---|---|---|---|
| 5,176,645 A * | 1/1993 | Guerrero | ............... | A61M 5/204 |
| | | | | 604/150 |
| 5,509,904 A | 4/1996 | Kilham | | |
| 5,540,657 A | 7/1996 | Kurjan | | |
| 5,593,388 A | 1/1997 | Phillips | | |
| 9,393,370 B2 | 7/2016 | Auld et al. | | |
| 2004/0035491 A1 | 2/2004 | Castellano | | |
| 2004/0049151 A1 * | 3/2004 | Lell | ......................... | A61M 5/30 |
| | | | | 604/72 |
| 2009/0299328 A1 | 12/2009 | Mudd et al. | | |
| 2015/0051574 A1 | 2/2015 | Tan | | |
| 2016/0361496 A1 | 12/2016 | Guillermo et al. | | |
| 2018/0028761 A1 * | 2/2018 | Anand | ............... | A61M 5/2033 |
| 2018/0132990 A1 | 5/2018 | Baeten et al. | | |
| 2018/0168789 A1 * | 6/2018 | Shiku | ................... | A61K 9/0019 |
| 2018/0304017 A1 * | 10/2018 | Edwards | ................ | A61M 5/24 |
| 2023/0158248 A1 | 5/2023 | Menz | | |

FOREIGN PATENT DOCUMENTS

| | | | |
|---|---|---|---|
| CN | 102497899 A | 9/2014 | |
| CN | 105797244 A | 7/2016 | |
| CN | 208301963 U | 1/2019 | |
| CN | 109310409 A | 2/2019 | |
| CN | 106573108 A | 11/2019 | |
| DE | 69525567 T2 | 10/2002 | |
| EP | 0810890 B | 11/2002 | |
| EP | 2090218 B1 | 9/2012 | |
| FR | 2714834 A1 | 7/1995 | |
| JP | 2013085911 A | 5/2013 | |
| NL | 7008369 A | 12/1971 | |
| WO | 02/076542 A1 | 10/2002 | |
| WO | 2011/022611 A2 | 2/2011 | |
| WO | 2022/112088 A1 | 6/2022 | |

OTHER PUBLICATIONS

International Search Report dated Feb. 11, 2022, for PCT/EP2021/082143, filed Nov. 18, 2021.

Written Opinion for PCT/EP2021/082143, filed Nov. 18, 2021.

Result of Examination Report for German Patent Application No. No. 20 2020 106 870.9 filed Nov. 30, 2020.

International Preliminary Report on Patentability dated Mar. 8, 2022, with Written Opinion for PCT/EP2020/073645 filed Aug. 24, 2020.

International Preliminary Report on Patentability dated May 30, 2023 and Written Opinion for PCT/EP2021/082143 filed Nov. 18, 2021.

Chinese Patent Office Action dated Mar. 18, 2024 for Chinese Patent Application No. 202080011207.2.

International Search Report dated Oct. 16, 2020 for PCT/EP2020/073645 filed Aug. 24, 2020.

Written Opinion for PCT/EP2020/073645 filed Aug. 24, 2020.

Result of Examination Report for German Application No. 10 2019 123 870.6 filed Sep. 5, 2019.

\* cited by examiner

PEN-LIKE SYRINGE SYSTEM

FIELD OF THE DISCLOSURE

The disclosure relates to a pen-like syringe system.

BACKGROUND

Syringe systems are used in medicine in numerous and different areas of application. In addition to the general requirements, which are supposed to ensure reliability and safety of the syringe systems, user friendliness, in particular safe and convenient holding, guiding and operation of the syringe system are also of significance.

European patent EP 0 810 890 B1 discloses a pen-like electronic syringe system with an elongated housing. An ampule with a syringe plunger movable therein can be inserted into a front area of the syringe system. Actuation of the syringe plunger occurs via a battery-operated drive system. Operation of the syringe system is then controlled via control switches.

US patent application US 2018/132990 A1 shows a syringe system in which liquid is fed to a needle provided for delivery of the liquid by a pump from a liquid container mounted on the device.

SUMMARY

One aspect of the disclosure relates to an ergonomic syringe system with a syringe holder provided for a syringe, which enables simple and reliable holding, guiding and operation of the syringe system, in particular irrespective of the hand size of a user, safe and targeted injection of a substance or removal of a substance, in particular injection into or removal from a human or animal body, thereby preventing possible contamination of the substance being injected or removed and ensuring easy insertion of a syringe into the syringe holder and the removal thereof.

A syringe is understood to mean a device having a syringe barrel (or primary container), in particular a cylindrical syringe barrel, in which a plunger is movably guided (in particular without a plunger rod) and which has a connection device, for example, a nozzle and/or cannula, on the front (proximal) end. The term syringe then also includes so-called carpules and cylindrical ampules with a perforable membrane on the front (proximal) end thereof.

A pen-like syringe system is disclosed herein. Appropriate embodiments and advantageous modifications are also disclosed herein.

A pen-like syringe system is understood to mean an essentially elongated syringe system that can be held by the user in one hand, like a pen. The pen-like syringe system is ordinarily held, guided and operated with two fingers (the term finger also including the thumb), in particular between the thumb and index finger, or with three fingers, in particular between the thumb, index finger and middle finger.

The pen-like syringe system according to the disclosure includes a syringe holder, which is configured to accommodate a syringe. A syringe insertable into the syringe holder has a syringe barrel, in particular a cylindrical syringe barrel, and a plunger movably guided in the syringe barrel. At its front (proximal) end, the syringe can have a conical or (circular) cylindrical nozzle or a connection device, in particular a Luer connection (Luer Lock, Luer Slip) and/or a cannula. The pen-like syringe system also includes a drive housing connected to the syringe holder. The syringe holder forms the front (proximal) part and the drive housing the rear (distal) part of the syringe system. An electric delivery device operated by an integrated power supply is arranged in the drive housing according to the disclosure for (pneumatic) operation of the plunger of a syringe introduced into the syringe holder with pressure or negative pressure, in particular for direct action on the plunger by pressure or negative pressure. The delivery device is then connected (pneumatically) via a drive channel to the plunger of a syringe inserted into the syringe holder and can be operated via a button arranged on the syringe system. The pen-like syringe system also has a vent channel with a first end connected to the drive channel and a second end connected via an opening to the surroundings, the opening being closeable during activation of the button.

The syringe system can then be used in particular for medical purposes, in particular for ophthalmology. The syringe system can consist of materials suitable for medical purposes, in particular plastics suitable for medical purposes. This enables simple sterilization, for example, by steam or x-rays or UV radiation or ethylene oxide.

The pen-like syringe system according to the disclosure offers an ergonomic syringe system that enables simple and convenient operation of the syringe system, in particular irrespective of the hand size of the user, in addition to simple and safe holding and guiding. The syringe system guarantees safe and targeted injection of a substance or removal of a substance, in particular into or from a human or animal body. The pen-like syringe system can be held like a pen between the thumb and index finger or between the thumb, index finger and middle finger. The syringe system can be held, guided and operated close to the front end of a syringe inserted into the syringe holder, for example, close to a cannula of the syringe, facing away from the drive housing. This ensures safe and proper guiding of the syringe system and simple handling of the syringe system. Any necessary change in position of the syringe system during injection or during removal, in particular a change in position of the tip of a cannula, is then simply and advantageously possible by withdrawing or introducing the cannula tip into the human or animal tissue, in particular during both injection and substance removal. A change in the position of the syringe system or a cannula tip is required, for example, in the field of ophthalmology, when a perfluorocarbon bubble is to be positioned in the eye.

The button can be activated, for example, using the index finger. Only the force required to activate the button then need be applied for injection or removal of a substance. In comparison with ordinary syringes, in which manual operation of a plunger rod connected to the plunger of the syringe is required, the pen-like syringe system is simple and convenient to operate. In particular, a large force or strong pressure need not be applied to operate the syringe system. This ensures safe holding and guiding of the syringe system, in particular during injection or removal. It is also conceivable that the force to be applied to activate the button can be adjusted via a device arranged on the syringe system, for example, depending on the desired force to be applied by the user to activate the button. The force acting on the plunger and therefore the injection or removal rate can likewise also be limited by a device.

In the syringe system according to the disclosure, apart from action on the plunger by pressure or negative pressure, no additional media connection to the plunger, for example, through a plunger rod or hydraulic delivery medium, etc. is present. There is no risk of possible contamination of a substance being injected or removed, the substance only being connected to the plunger of the syringe, in addition to the interior of the syringe barrel.

The configuration of the pen-like syringe system, in particular exposure of the piston of the syringe inserted into the syringe holder to pressure or negative pressure through the delivery device operable via the button, also enables precise dosing of the injection or removal of a substance. Injection in any doses, for example, dropwise or in a continuous stream, is then possible. Continuous injection is then also ensured without hang-up of the plunger, which occurs in known syringe systems, for example, owing to non-homogeneous silicone coating of the syringe and/or because of jamming or sticking of the plunger on the syringe barrel. The same also applies for removal of a substance.

The action of pressure or negative pressure on the plunger of a syringe inserted into the syringe holder of the syringe system according to the disclosure only occurs if the opening arranged on the second end of the vent channel is closed. Otherwise, the drive channel, which is connected to the first end of the vent channel, for example, via a connection piece designed as a T-piece, is connected to the surroundings. The action of pressure or negative pressure on the plunger and therefore movement of the plunger relative to the syringe barrel is thereby prevented or stopped immediately. The design of the syringe system therefore ensures direct and immediate termination of an injection or removal as soon as activation of the button has ended or the opening of the vent channel is not (or no longer) closed. Immediate release of a pressure or negative pressure previously acting on the plunger occurs immediately through the vent channel. Possible "trailing off" or final dripping of an injection or removal of a substance because of an otherwise existing pressure reservoir is therefore not possible.

In a preferred embodiment of the syringe system, the opening of the vent channel can be closed by a finger activating the button. If the button is not activated or improperly activated, for example, unintentional touching of the button or incorrect positioning of the finger prescribed for activation of the button or improper handling of the injection system, the opening of the vent channel is not closed. Unwanted or uncontrolled action of pressure or negative pressure on the plunger or unwanted or uncontrolled injection or removal is therefore prevented. In a particularly preferred embodiment, the opening can be automatically closed by the finger during manual activation of the button with a finger. The opening of the vent channel is in particular positioned so that the operator closes it during proper activation of the button and proper handling of the syringe system. In addition to the above-mentioned advantages and design advantages of such an embodiment, proper handling of the syringe system is also thereby ensured. By closing the opening of the vent channel with a finger activating the button, termination of an injection or removal is also ensured immediately, on termination of activation of the button by the finger activating the button, and therefore reliable injection or removal without trailing off effects.

In an advantageous embodiment, the electric delivery device can be a diaphragm pump and/or the plunger of a syringe inserted into the syringe holder can be acted upon with air. The diaphragm pump forms a micropneumatic system or part of a micropneumatic system integrated into the syringe system. The use of a diaphragm pump and the use of air as a driving medium enables the plunger to be operated in a particularly simple and advantageous fashion. A mechanical device that is connected to the plunger to move it is then not required. By using the diaphragm pump and action of air on the plunger, complex and error-prone gear mechanisms between the delivery device and the plunger are therefore unnecessary. Diaphragm pumps are also very robust and insensitive to disturbances.

The drive housing preferably has at least one supply opening or a supply channel connected to the delivery device to connect the delivery device to the surroundings or a gas reservoir. Adequate supply of the delivery device, in particular a diaphragm pump, with air or a gas (mixture) situated in a gas reservoir is thereby ensured. The possible build-up of pressure developing in a drive housing or negative pressure is thus prevented during operation of the delivery device. The supply opening is preferably arranged on the drive housing so that it is not closed by the hand of the user during operation of the syringe system. It is also conceivable that the supply opening or supply channel has a filter element, for example, for purification of the air used as the delivery medium.

In a particularly preferred embodiment, the syringe holder is hinged to the drive housing in a tiltable manner. Particularly simple and rapid insertion and removal of a syringe into or from the syringe holder is thereby enabled. By inserting or removing a syringe into or from the syringe holder, there is also no transfer of a substance into or from a syringe firmly connected to the syringe system and no risk of the problems associated therewith, for example, the risk of possible contamination of a substance being injected or removed. In a particularly advantageous manner, the drive housing or the syringe holder can have a locking lever for releasable fastening of the syringe holder to the drive housing or vice versa. In an alternative embodiment, the syringe holder can be connected to the drive housing releasably via a bayonet lock or a thread. A simply designed, robust and user-friendly configuration of the syringe system is provided both by the locking lever and by the bayonet lock and thread, enabling simple locking and unlocking of the connection of the syringe holder and drive housing and therefore rapid and simple insertion or removal of a syringe into or from the syringe holder. For a tight connection, in particular for a gas- or air-tight connection of the drive housing to the syringe holder or a syringe inserted into the syringe holder, the drive housing can have a sealing element on its front (proximal) end, in particular an O-ring.

The syringe holder can advantageously be at least partially transparent and/or have at least one laterally arranged window through which a syringe arranged in the syringe holder is at least partially visible. The filling level of the syringe or the progress of an injection or removal can thus be observed. For example, a removed substance or possibly air bubbles present in the syringe, etc. are also visible, which indicate leaks or other difficulties during injection or removal so that possible corrections can be made or, if necessary, interruption of the injection or removal.

In a preferred embodiment of the syringe system, the button can be arranged on the syringe holder, in particular close to the front end of the syringe holder facing away from the drive housing. The resulting arrangement of the finger used to operate the syringe system close to the front end of the syringe, for example close to a cannula mounted on the syringe, therefore enables reliable guiding of the syringe system, in particular when the button is activated at the same time.

In an advantageous embodiment, the opening of the vent channel can be arranged in the button or the syringe holder can have a recessed area in which the button and opening of the vent channel are arranged, in which case the opening of the vent channel points essentially in a longitudinal direction of the syringe system running through the drive housing and syringe holder, in particular in the direction of the front end of the syringe holder, and activation of the button occurs perpendicular to the longitudinal direction. An opening provided in the button can in particular point upward, i.e., in the activation direction or movement direction of the finger activating the button. A syringe system ensuring that the opening of the vent channel is (automatically) closed during activation of the button by a finger activating the button is provided by the described embodiments and arrangements of the opening.

In a further advantageous embodiment, the syringe system can be designed to be heatable in the area of the syringe holder. This embodiment is advantageous, for example, during injection of substances having a higher viscosity, in order to facilitate injection by heating the substance to be injected.

The syringe system can preferably be designed as a closed, compact syringe system. Lines connected to the syringe system or similar connections that would hamper or interfere with the use or handling of the syringe system are not present. The compact design in particular provides a reliable, ergonomically advantageous and user-friendly syringe system. The closed design is advantageous, for example, in order to prevent contamination of the syringe system, in particular contamination of the interior of the syringe system by external influences.

The integrated power supply can advantageously be a battery or an accumulator arranged in or on the drive housing. The integrated power supply, for example, can be incorporated into a receptacle arranged on the rear (distal) end of the drive housing, i.e., on the end of the drive housing facing away from the syringe holder. The receptacle for the integrated power supply is then preferably readily accessible from the outside. Simple replacement of a battery used as an integrated power supply is thereby enabled. In a particularly advantageous embodiment, the syringe system can have a connection element for charging the integrated power supply, in particular for charging a battery used as an integrated power supply. The connection element can then be a USB connection. The connection element is then preferably arranged in the drive housing. By using an integrated power supply, an injection system is provided that requires no external connections, in particular power cables, etc. that would adversely affect or interfere with use or handling of the syringe system. In a further advantageous embodiment, the integrated power supply, in particular batteries used as an integrated power supply, can be arranged in a separate power supply unit that is releasably connectable to the syringe holder or drive housing via a quick-change system, for example, by snapping on. This enables rapid replacement of the integrated power supply and charging of batteries used as an integrated power supply, independently of the syringe system. The power supply unit can then be arranged, for example, at different, ergonomically suitable positions of the syringe system. In addition to arranging the power supply unit on the rear (distal) end of the drive housing, lateral arrangement of the power supply unit on the syringe system or drive housing is also conceivable. Separate embodiments for right-handed and left-handed persons are then also conceivable, in which case the power supply unit is arranged on different sides of the syringe system.

In an advantageous embodiment, the syringe system can have a device for adjusting or limiting the pressure or negative pressure produced by the delivery device, in particular the injection rate and/or the removal rate caused thereby. Adaptation of the syringe system and the power of the delivery device to the corresponding requirements of an injection or removal is thus possible. It is also conceivable that the syringe system has a device, in particular a switch, via which alternating action of pressure or negative pressure on the plunger can be carried out selectively. This results in a syringe system that can be used both for injection and for removal.

The syringe system can preferably have a display element for direct or indirect display of the pressure or negative pressure acting on the plunger or the force acting on the plunger and/or to display the charge status of the integrated power supply. With particular preference, the display device can be an optical display that indicates the power of the delivery device and/or the power tapped by the delivery device and/or the pressure or negative pressure acting on the plunger and/or the charge status of the integrated power supply. Monitoring of an ongoing injection or removal, as well as monitoring of the status or settings of the syringe system as well as the charge status of the integrated power supply are thereby possible. The settings and status of the syringe system can therefore be monitored before an injection or removal and also during an injection or removal.

In an advantageous embodiment, the syringe system can have a mechanical restraining device that prevents loosening of the cannula that is mounted on a syringe barrel of a syringe inserted into the syringe holder. A cannula can then be mounted in particular on a nozzle having a Luer Lock, for example, arranged on the front end of a syringe. The cannula then includes a hollow needle and a cannula connection. The cannula connection is a device provided for connection of the cannula to the syringe or a nozzle to the syringe, which can have a Luer Lock, in particular, and which carries the hollow needle. Unwanted loosening of the cannula from the syringe, in particular during injection or removal, and/or insertion of a syringe with an improperly mounted cannula into the syringe holder, are prevented by the restraining device. The restraining device is arranged at the front end of the syringe holder, i.e., at the end of the syringe holder facing away from the drive housing, or forms the front end of the syringe holder. The restraining device has a passage through which the hollow needle of a cannula extends. In order to prevent unwanted loosening of the cannula from the syringe, the restraining device is configured so as to be guided at least partially over the cannula connection of a syringe inserted into the syringe holder, or at least partially encloses the cannula connection. The restraining device therefore forms a stop element against which the cannula connection of a syringe inserted into the syringe holder rests. For example, the restraining device can be a passage (or hole) tapering in the direction of the front (proximal) end of the syringe system, in which the cannula connection is clamped and/or prevents movement of the cannula in the direction of the front end of the syringe system and therefore loosening of the syringe inserted into the syringe holder.

In another embodiment, the drive channel and/or the vent channel can include a tube connection or be configured as a tube connection. This enables a configuration of the drive and vent channel that is simple to design and manufacture or a connection for the drive channel with the delivery device and the vent channel with the drive channel that is advantageous to design and manufacture. The drive and vent channels configured as a tube connection can then be simply connected to each other via a connection piece, for example, a T-shaped connection piece.

The syringe system can preferably be configured so as to be suitable for medical purposes, in particular for ophthalmology. With particular preference, the syringe system is made from sterilizable materials, like aluminum, stainless steel, plastics that are stable during sterilization or combinations thereof. Advantageously, the syringe system is then configured so that the surfaces of the syringe holder and the drive housing or its individual elements enable sufficient contact with a sterilizable medium or are accessible to a sterilizable medium, like steam or radiation sterilization. The required cleaning or sterilization of the syringe system before and/or after use of the syringe system is therefore made possible in a simple and advantageous manner.

The syringe system preferably includes a syringe inserted into the syringe holder, in which case the syringe has a syringe barrel and a plunger movable in the syringe barrel. The syringe can also have a nozzle on the front (proximal) end, in particular a conical or (circular) cylindrical nozzle, or a connection device, in particular a Luer connection (Luer Lock, Luer Slip) and/or a cannula. The syringe can have a flange on the rear (distal) end, which, when a syringe inserted into the syringe holder, is arranged in a flange receptacle of the syringe holder provided for the flange.

BRIEF DESCRIPTION OF THE DRAWINGS

These and other features, as well as advantages and effects of the pen-like syringe system according to the disclosure will become apparent from the following illustrative embodiments described in greater detail below with reference to the accompanying drawings. The drawings show.

DETAILED DESCRIPTION

Figure 1:
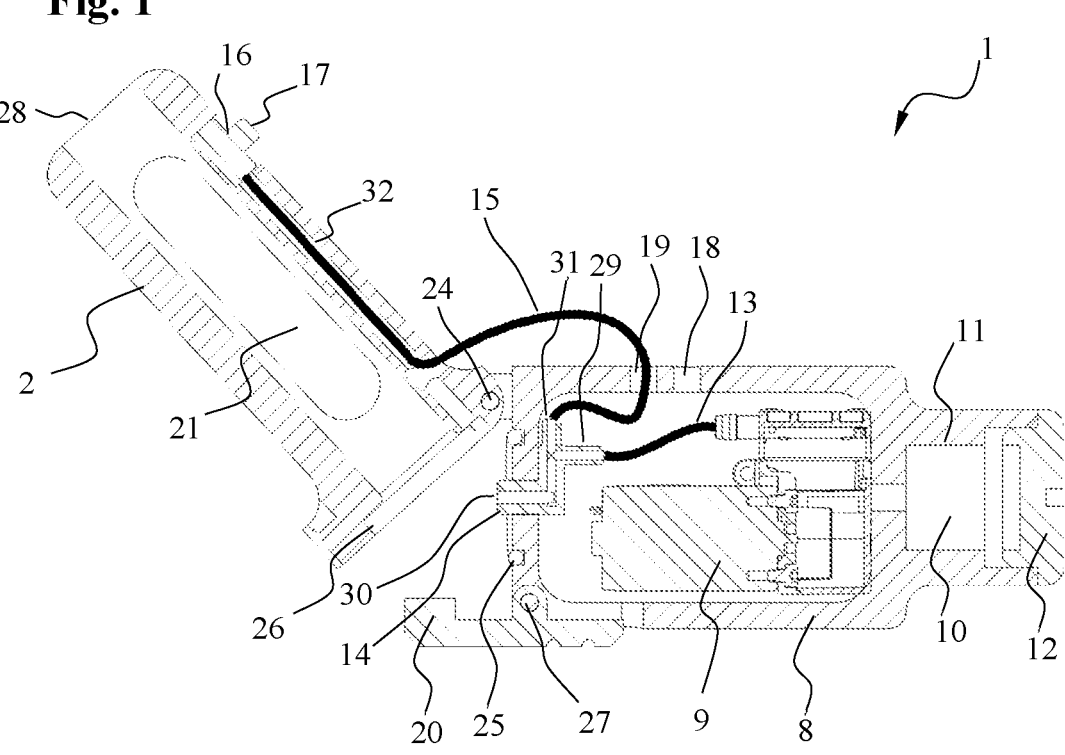
FIG. 1 a longitudinal section of the first embodiment of a pen-like syringe system according to the disclosure in the tilted-up position without a syringe inserted into the syringe holder.

A first illustrative embodiment of a pen-like syringe system 1 according to the disclosure is shown in FIG. 1 to FIG. 6 in different (sectional) views. The syringe system 1 has a syringe holder 2, which is connected via a joint 24 to a drive housing 8 or hinged thereto. The syringe holder 2 can be firmly connected to the drive housing 8 or locked in the closed position provided for use of the syringe system 1 for injection or removal via a locking lever 20 arranged on the bottom of the drive housing 8. The closed position of the syringe system 1 is shown, for example, in FIG. 3 and FIG. 4. The lock that exists between the syringe holder 2 and the drive housing 8 in the closed position of the syringe system 1 can be unlocked by operating the locking lever 20 so that the syringe system 1 can be brought into the tilted-up position shown in FIG. 1 and FIG. 2.

Figure 2:
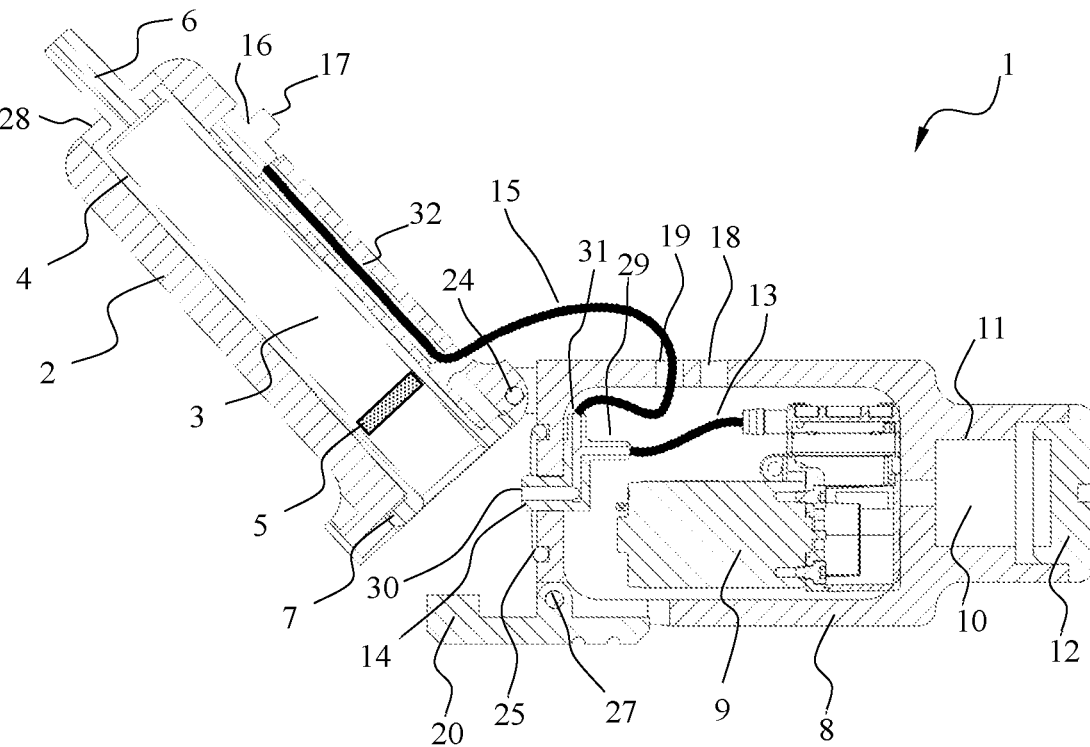
FIG. 2 a longitudinal section of the syringe system from FIG. 1 with a syringe inserted into the syringe holder.

The syringe holder 2 is designed to accommodate a syringe 3. In the tilted-up position of the syringe system, with the syringe holder 2 empty, as shown in FIG. 1, a syringe 3 can be inserted into the syringe holder 2 via the rear side of the syringe holder 2 facing the drive housing 8. The syringe system 1 with a syringe 3 inserted into the syringe holder 2 is shown in FIG. 2, for example. The syringe 3 has a cylindrical syringe barrel 4 and a plunger 5 that is movably guided in the syringe barrel 4. At its front (proximal) end, the syringe 3 has a nozzle 6, which is guided in the syringe 3 inserted into the syringe holder 2 through a passage 28 at the front end of the syringe holder 2, i.e., the end of the syringe holder 2 facing away from drive housing 8. The nozzle 6, which in particular can be designed cylindrical or conical, can have a connection device, in particular a Luer connection (Luer Lock, Luer Slip) for connection of a cannula. The syringe 3 has a flange 7 at its rear (distal) end, which is arranged in a flange receptacle 26 provided for the flange 7 when the syringe 3 is inserted into the syringe holder 2. In the closed position of the syringe system 1, the flange 7 of the syringe 3 is then forced against the front end of the drive housing 8 facing the direction of the syringe holder 2, as shown, for example, in FIG. 3. For this purpose, the drive housing 8 has a sealing element 25 at the front end, in particular a sealing ring, against which the flange 7 is pressed when the syringe system 1 is in the closed position. A tight connection is thereby created between the syringe 3 and flange 7 and drive housing 8. Exact and secure positioning of the syringe 3 in the syringe holder 2 is also ensured via the arrangement of the flange 7 in the flange receptacle 26.

When an injection is to be made, for example an ophthalmological injection of perfluorocarbons into the eye of a patient, the syringe 3 inserted into syringe holder 2 is filled with the substance to be injected. The substance to be injected is then arranged in the syringe barrel 4 of the syringe 3 between the nozzle 6 and the plunger 5. During a removal, on the other hand, the syringe 3 inserted into the syringe holder 2 is not filled. The plunger 5 is then initially arranged at or close to the nozzle 6. The syringe system 1, in particular the syringe holder 2, is designed according to the size of a syringe 3 to be inserted into syringe holder 2. For example, the syringe system 1 or the syringe holder 2 can be designed to accommodate standard syringes known for injection or removal, which can hold 2.25 mL (which are used, for example, for the injection of dyes), or 5 mL, or 10 mL (which, for example are to be used for the injection of perfluorocarbons or silicone oils).

Figure 4:
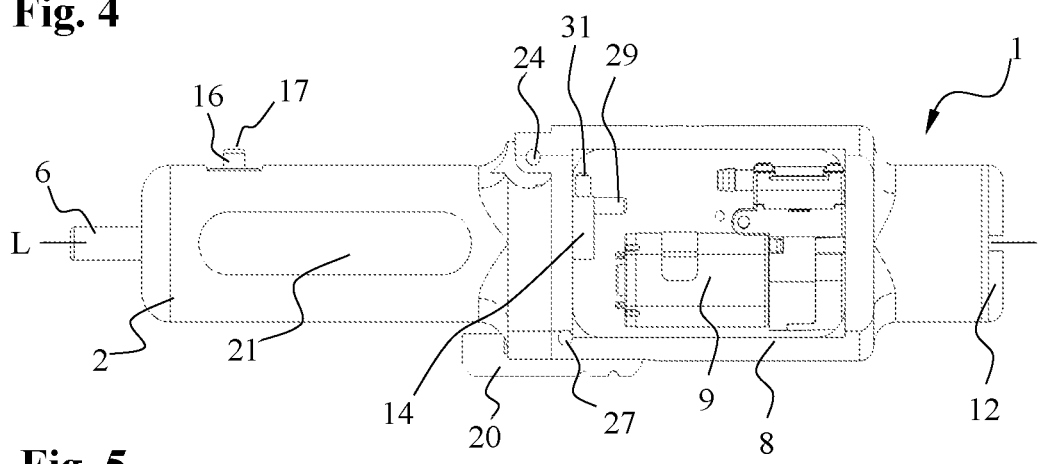
FIG. 4 a partially cut-away side view of the syringe system of FIG. 1 in the closed state with a syringe inserted into the syringe holder.
Figure 5:
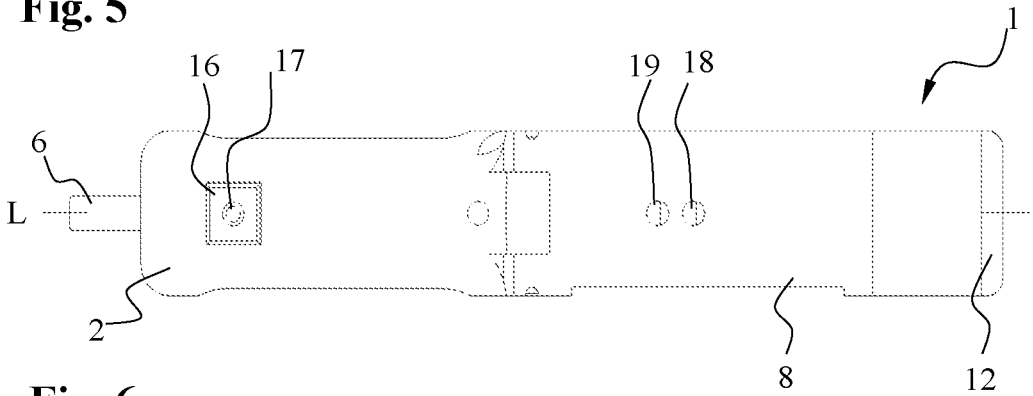
FIG. 5 a top view of the syringe system from FIG. 1 in the closed state and with a syringe inserted into the syringe holder.

The syringe holder 2 of the first illustrative embodiment of a syringe system 1 has a window 21 on each side, as shown, for example, in FIG. 1 and FIG. 4. A syringe 3 arranged in the syringe holder 2 is at least partially visible through the window 21. Because of this, the filling level of the syringe 3 or the progress of an injection or removal can be observed. For example, a removed substance or possibly air bubbles present in the syringe 3, etc. are as a result also visible, indicating difficulties existing during injection or removal.

An electric delivery device 9 and an integrated power supply 10 for supplying the delivery device 9 with current or power are arranged in the drive housing 8. The electric delivery device 9 is preferably a diaphragm pump and the power supply 10 connected thereto is preferably an accumulator or a battery. The power supply 10 in the illustrative embodiment shown in FIGS. 1 to 6 is arranged in a receptacle 11 arranged at the rear end of the drive housing 8, i.e., the end of the drive housing 8 facing away from syringe holder 2. The receptacle 11 is then closed by a cover 12, which is releasably connected to the holder 11, for example, by a thread. The described configuration described enables a simple replacement of the integrated power supply 10. It is also conceivable that the drive housing 8 has a connection element for charging a battery used as power supply 10. The connection element can in particular be a USB connection or another suitable electrical connection.

The delivery device 9 is activated via a button 16 in the front area of the syringe holder 2 close to the nozzle 6 of a syringe 3 inserted into the syringe holder 2. The button 16 is activated perpendicular to a longitudinal direction L of the syringe system 1 running through the drive housing 8 and the syringe holder 2 in the closed state of the syringe system 1. The button 16, which is arranged on the top of the syringe holder 2 opposite the locking lever 20, is connected for this purpose to the delivery device 9 via an (electrical) connection not shown.

The delivery device 9 has a drive channel 13 for (pneumatic) operation of the plunger 5 of a syringe 3 inserted into the syringe holder 2 when the syringe system 1 is closed with pressure or negative pressure. Air, in particular, is then used as a driving medium to operate the plunger 5 with pressure. To supply a diaphragm pump used as the delivery device 9 with sufficient air and to prevent any pressure or negative pressure that might develop in the drive housing 8 during operation of the delivery device 9, the drive housing 8 has a supply opening 18 on the top, which is connected to the surroundings.

Figure 3:
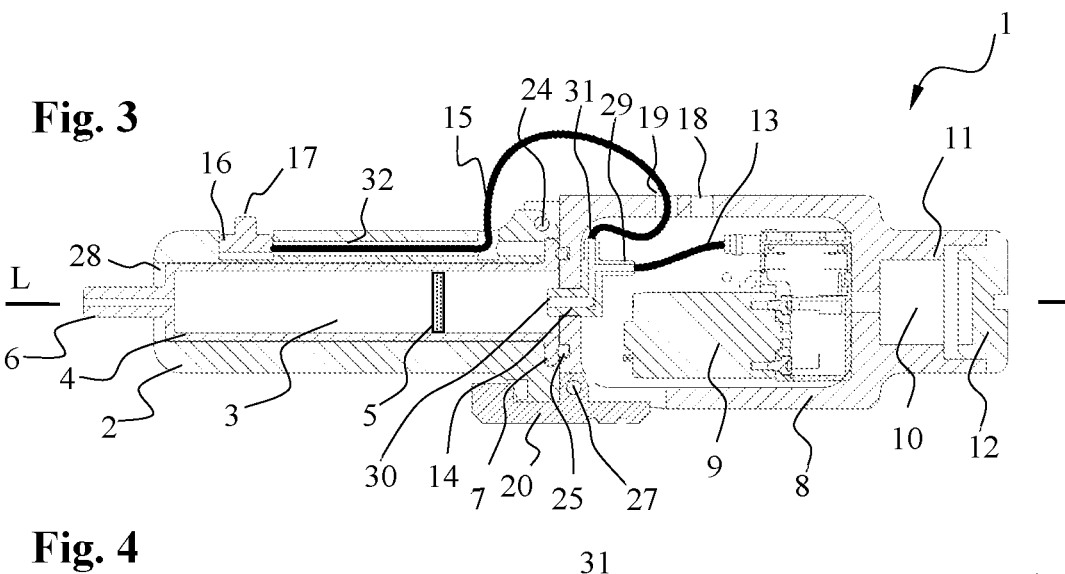
FIG. 3 a longitudinal section of the syringe system of FIG. 1 in the closed state with a syringe inserted into the syringe holder.
Figure 6:
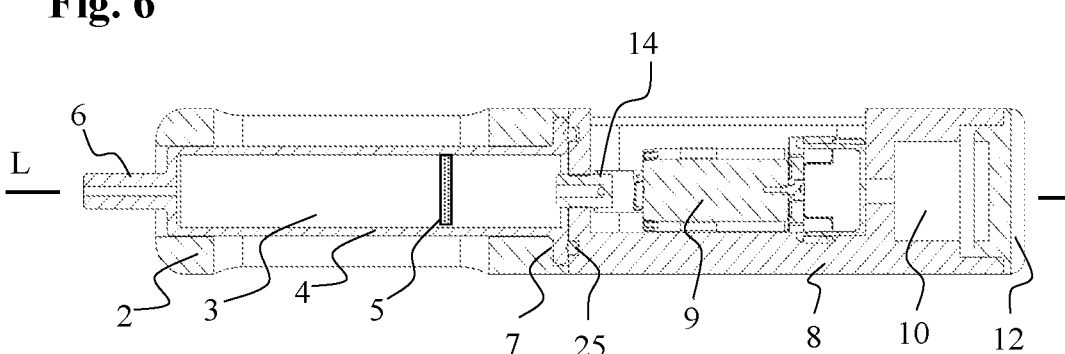
FIG. 6 a cross section at the height of the delivery device through the top view shown in FIG. 5.
Figure 7:
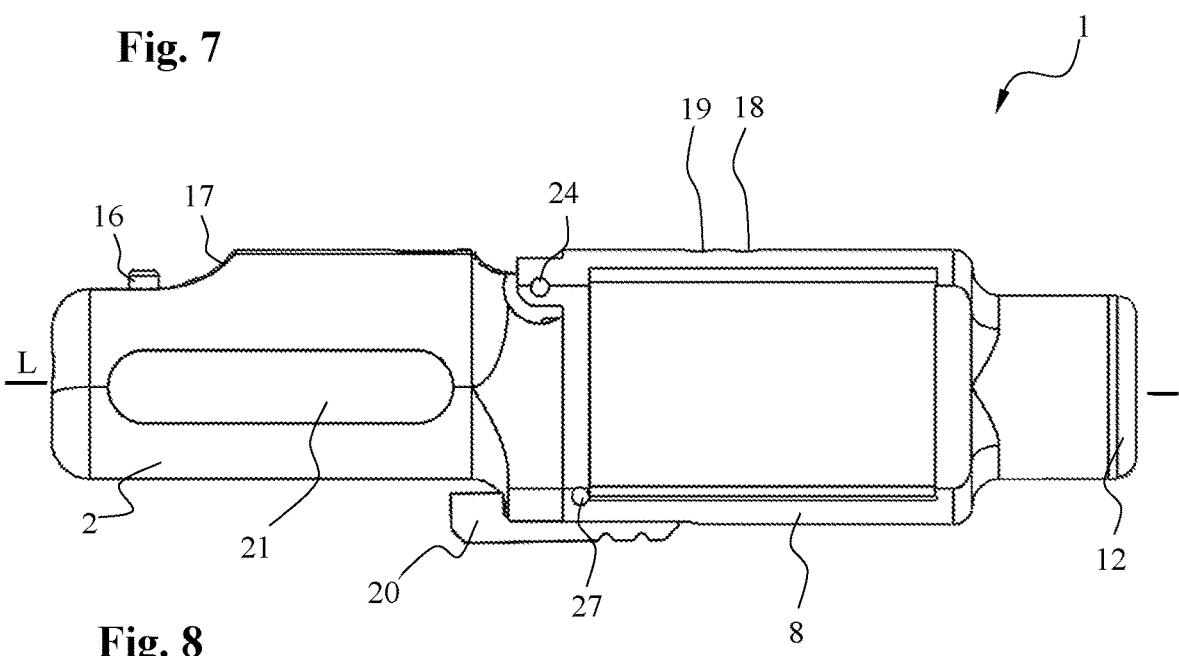
FIG. 7 a side view of a second embodiment of a pen-like syringe system according to the disclosure in the closed position without a syringe inserted into the syringe holder.
Figure 8:
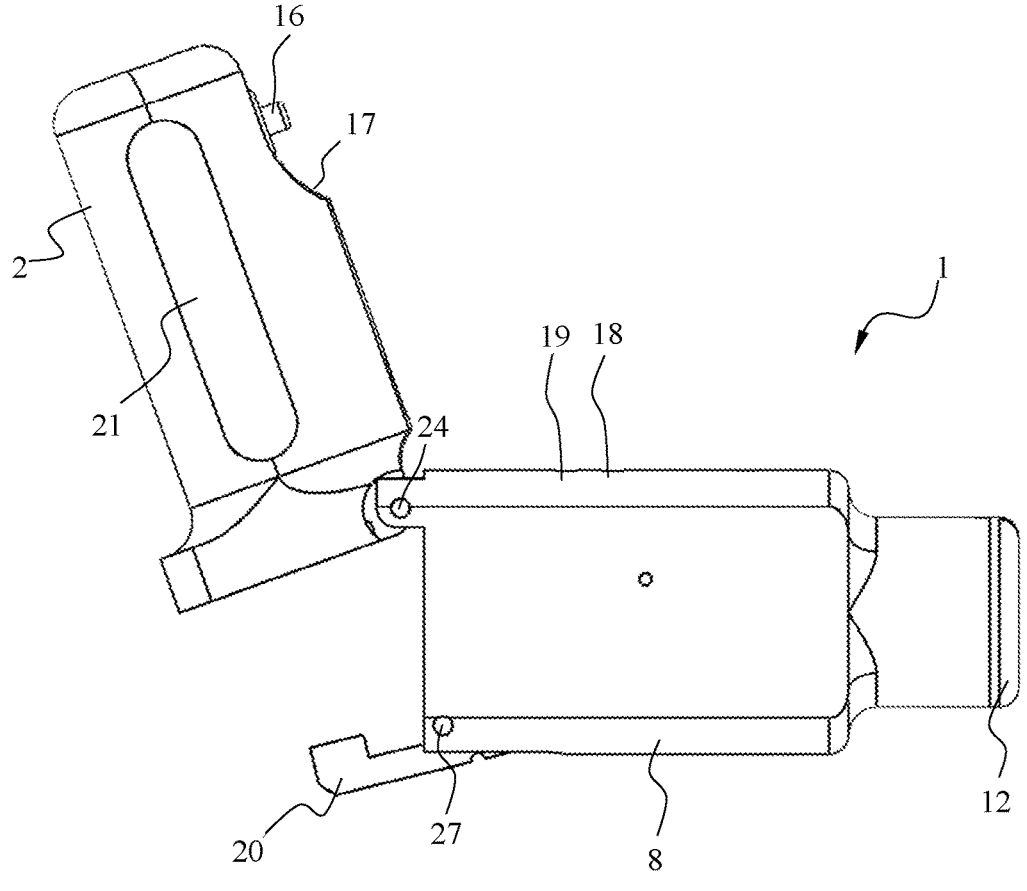
FIG. 8 a side view of the syringe system of FIG. 7 in the tilted-up position.

The drive channel 13 configured as a tube connection and shown in FIG. 1 to FIG. 3 is connected to a first input 29 of a connection piece 14 arranged at the front end of the drive housing 8. The connection piece 14 has a second input 30 on the side facing the direction of the syringe holder 2, which points in the direction of the plunger 5 of a syringe 3 inserted into the syringe holder 2 in the closed position of the syringe system 1. The second input 30 extends somewhat into the syringe barrel 4 of the syringe 3, as shown, for example, in FIG. 3 and in FIG. 6. FIG. 6 shows another longitudinal section of the syringe system 1 through the delivery device 9 in the second input 30. The connection piece 14 also has, as shown in FIG. 3, a third input 29 [sic; 31], which is connected to a first end of the vent channel 15. The vent channel 15 shown in FIG. 1 to FIG. 3 is designed as a tube connection. The second end of the vent channel 15 is connected to an opening 17 connected to the surroundings, which in the illustrative embodiment shown extends centrally through the T-shaped button 16 in longitudinal section, as indicated in particular in FIG. 5. For the sake of simplicity, the vent channel 15 configured as a tube connection and the drive channel 13 are not shown either in FIG. 5, which shows a top view of the illustrative embodiment, or in FIG. 4, which shows the illustrative embodiment in a partially cut-away view. The vent channel 15 connected to the third input 31 of the connection piece 14 or the tube connection used in this case is guided from drive the housing 8 and then into a guide channel 32 via a recess 19, which is arranged on the top of syringe holder 2, and which is formed up to the opening 17, and connected to said opening 17.

Operation and use of the syringe system 1 is described below with reference to an injection to be made. In this case, a syringe 3 filled with a substance to be injected is inserted into the syringe holder 2 and the syringe system 1 is in its closed position intended for operation.

When the injection is to be carried out, the diaphragm pump used as delivery device 9 is activated by activating the button 16 with a finger of the user activating the button 16, for example, the index finger. During proper handling of the syringe system 1 and proper activation of the button 16 by the finger activating the button 16, the opening 17 is automatically and forcibly closed. The air used as a drive medium is fed via the drive channel 13 in the direction of the plunger 5 through the connection piece 14. When the opening 17 is closed, which is connected via the vent channel 15 to the connection 14 and therefore also to the drive channel 13 of the plunger 5, pressurization of the plunger 5 occurs. The plunger 5, which is movable in the syringe barrel 4, is therefore moved in the direction of the nozzle 6 whereby the substance contained in the syringe 3 is delivered from the nozzle 6 or a cannula attached thereto. When the opening 17 is not closed, for example, during improper activation of the button 16, or if activation of button 16 is terminated, the drive channel 13 and the plunger 5 are connected to the surroundings. Pressurization of the plunger 5 does not occur owing to air escaping through the opening 17. When activation of the button 16 has ended, an immediate termination of the injection is thus ensured, in particular without any trailing off effect. It is also ensured that no injection occurs during improper or uncontrolled activation of the button 16.

The above comments apply accordingly during removal of a substance (not further described), for example, from a human body, in which case the plunger 5 is acted upon with negative pressure instead of pressure.

Figures 11, 12:
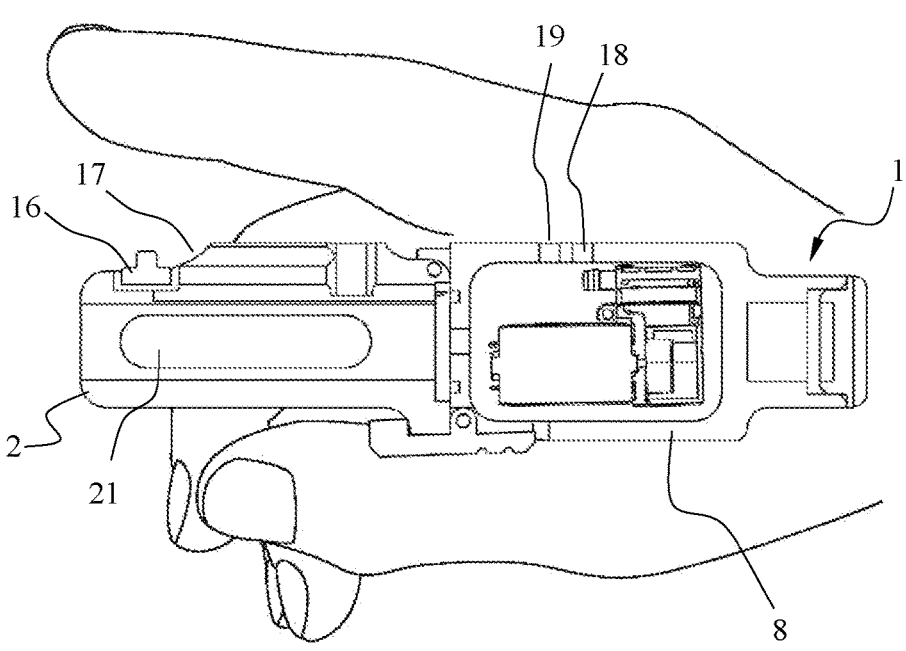
FIG. 11 a sketch of the handling of the syringe system of FIG. 7.
FIG. 12 a longitudinal section through a third embodiment of a syringe system according to the disclosure in the closed position with an inserted syringe.

A second illustrative embodiment of the pen-like syringe system 1 according to the disclosure is shown in different views in FIG. 7 to FIG. 11. FIG. 11 sketches the handing of the syringe system 1, the syringe system 1 being shown in a partial cut-away view. The reference numbers used to describe the second illustrative embodiment are used according to the reference numbers of the first illustrative embodiment.

The syringe system 1 shown in FIG. 7 to FIG. 11 corresponds essentially to the first illustrative embodiment shown in FIG. 1 to FIG. 6. No syringe 3 is inserted into the syringe holder 2 of the syringe system 1 shown in FIG. 7 to FIG. 11. The drive channel 13 configured as a tube connection similar to that of the first illustrative embodiment, and the vent channel 15 also configured as a tube connection as in the second illustrative embodiment are not shown for the sake of clarity. The connection piece 14 shown in the first illustrative embodiment is also not shown in the illustrative embodiment shown in FIG. 7 to FIG. 11. The connection piece 14 of the second illustrative embodiment can correspond to the connection piece 14 of the first illustrative embodiment or be a functionally equivalent T-piece for connecting the drive channel 13, vent channel 15 and plunger 5 (or the second input 30 of connection piece 14 pointing in the direction of plunger 5).

The illustrative embodiment shown in FIG. 7 to FIG. 11 differs from the first illustrative embodiment essentially in the configuration of the syringe holder 2 described below, in particular in the configuration or arrangement of the button 16 and the opening 17.

Figures 9, 10:
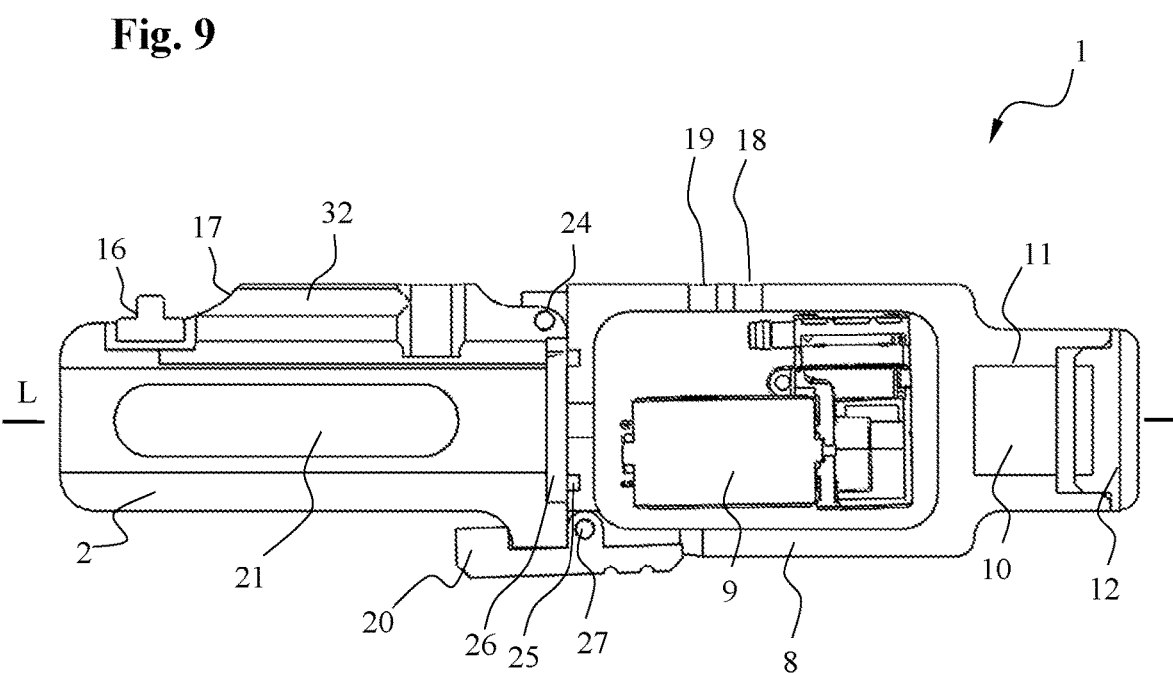
FIG. 9 a longitudinal section of the syringe system of FIG. 7.
FIG. 10 a top view of the syringe system of FIG. 7.

The syringe holder 2 of the second illustrative embodiment has a recessed area in the region of the front end of the syringe holder 2, in which the button 16 is arranged. The transition from the non-recessed area into the recessed area is formed by a rounded area, the button 16 being arranged close to this transition area. The opening 17 of the vent channel 15, as shown in particular in FIG. 10, is arranged in the transition area. The opening 17 points essentially in a longitudinal direction L of the syringe system 1 running in the direction through the drive housing 8 and syringe holder 2. The vent channel 15, in particular a vent channel 15 configured as a tube connection, whose second end is connected to the opening 17, runs at least in sections along a guide channel 32 running along the upper edge of the syringe holder 2. When the button 16 is properly activated, the finger operating the button 16, in particular the index finger of an operator, as shown for example in FIG. 11, rests on the opening 17 so that the opening 17 is automatically closed.

Handling of the pen-like syringe system 1, which is roughly the size of a human hand, is shown in FIG. 11. For the sake of clarity, not all reference numbers are included. In addition to activation of the button 16 and closure of the opening 17 via the index finger during activation of the button 16, the holding and guiding of the syringe system 1 with the thumb, index finger and middle finger are also shown. The syringe system 1 can be held, guided and operated in an ergonomically advantageous and reliable manner by an operator regardless of their hand size. FIG. 11 further indicates that the supply opening 18 is not closed by the hand of the operator during proper handling. The vent channel 15 designed as a tube connection and not shown in FIG. 11, which is guided on the top of the drive housing 8 through the recess 19 into the guide channel 32 of the syringe holder 2, and which therefore extends in sections beyond the syringe system 1, as shown for comparison in FIG. 4 of the first illustrative embodiment, also does not adversely affect operation of the syringe system 1.

A longitudinal section of a third illustrative embodiment of the pen-like syringe system 1 is shown in FIG. 12. The illustrative embodiment shown in FIG. 12 corresponds in its functional design largely to the previous illustrative embodiment. However, the special configuration of this illustrative embodiment, as described below, deviates partially from the preceding illustrative embodiment. The reference numbers used to describe the third illustrative embodiment shown in FIG. 12 correspond to the reference numbers of the first or second illustrative embodiment.

In contrast to the syringe holder 2 of the first two illustrative embodiments, which is hinged to the drive housing 8, the syringe holder 2 of the third illustrative embodiment is releasably connected to the drive housing 8 via a thread arranged at the rear end of the syringe holder 2. For this purpose, the drive housing 8 has a corresponding counter thread at its front end facing in the direction of the syringe holder 2. It is also conceivable to connect the syringe holder 2 to the drive housing 8 via a bayonet lock. The integrated power supply 10, in particular a battery, is also arranged in the in the drive housing 8 directly following a delivery device 9, in particular a diaphragm pump. A cover 12 releasably connected to the drive housing 8 is mounted on the rear end of drive housing 8. The cover 12 has a connection element 33 for charging the integrated power supply 10. The connection element 33 can in particular be a USB connection.

The syringe holder 2 also has a depression or trough in the front area in which the button 16 used to operate the delivery device 9 is arranged. The delivery device 9 is connected to a first input 29 of a T-shaped connection piece 14 via a drive channel 13 arranged at the front area of the drive housing 8. The second input 30 of the connection piece 14 faces in the direction of the plunger 5 of a syringe 3 inserted into the syringe holder 2. The connection piece 14 is connected via a third input 31 to a first end of a vent channel 15 running essentially along the upper edge of the syringe holder 2. The second end of the vent channel 15, which is connected to the surroundings via opening 17, is arranged in the area of the depression in which the button 16 is also arranged, in which case the opening 17 faces in the direction of the front end of the syringe holder 2 along the longitudinal direction L of the syringe system 1. The drive channel 13 and the vent channel 15 are formed by bores or short tubular connection elements running in the syringe holder 2 or in the drive housing 8. The tube connections used in the previous illustrative embodiments of the drive channel 13 or vent channel 15, in particular the tube connection of the vent channel 15 partially outside of the drive housing 8 or syringe holder 2, are not present here.

The syringe holder 2 of the third illustrative embodiment also has a mechanical restraining device 22 at its front end, which prevents loosening of a cannula mounted on the syringe barrel 4 of a syringe 3 inserted into the syringe holder 2, or loosening of a cannula mounted on a nozzle 6 of the syringe 3. A cannula (not shown in FIG. 12) has a hollow needle and a cannula connection. The cannula connection represents a device for connecting the cannula to the syringe 3 or to the nozzle 6 of the syringe 3, which carries the hollow needle. The restraining device 22 has a passage 28 through which a hollow needle of a cannula mounted on the syringe 3 is guided. The restraining device 22 is also designed so that it is guided at least partially via the cannula connection of a cannula mounted on the syringe 3 inserted into the syringe holder 2, or encloses the cannula connection. The restraining device 22 forms a stop element for the cannula connection. In the closed position of the syringe system 1, the cannula connection rests against the restraining device 22. The passage 28 of the restraining device 22 can be designed as a passage 28 tapering in the direction of the front (proximal) end of the syringe system 1 (not shown in FIG. 12), which clamps the cannula connection or prevents movement of the cannula connection, and therefore the cannula, in the direction of the front end of the syringe system 1. The restraining device 22 prevents unwanted loosening of a cannula from the syringe 3. In particular, loosening of a cannula during injection or removal is prevented. The mechanical restraining device 22 also prevents a syringe 3 with an improperly mounted cannula from being inserted into the syringe holder 2.

A simple and secure holding, guiding and operation of the syringe system 1 is provided by the configuration of the syringe system 1 according to the disclosure, in particular independently of the size of the hand of an operator, and therefore reliable and targeted injection or removal of substance. In syringe systems known from the prior art, there is a risk of possible contamination of the substance being injected or removed due to a plunger rod (lubricated mechanism) being connected to the plunger during its operation or to refilling of the substance being injected or removed from an external container into the syringe or vice versa; this risk does not exist in the syringe system 1 according to the disclosure. The syringe system 1 shown also enables simple and rapid insertion and removal of a syringe 3 into or from the syringe holder 2 through the syringe holder 2 hinged to the drive housing 8 or the syringe holder 2 releasably connected to the drive housing 8 via a thread or a bayonet lock. In particular, ordinary standard syringes (without finger flange and plunger rod) can be used in the syringe system 1 according to the disclosure. The syringe holder 2, in particular the size of the syringe holder 2 as well as the flange receptacle 26 is then configured according to the (standard) syringes 3 being used.

In addition to the illustrative embodiments shown in FIGS. 1 to 12, other variants of the pen-like syringe system 1 not shown in the drawing and devices additionally provided on the pen-like syringe system 1 are possible. For example, an embodiment is possible in which the syringe holder 2 is fully or partially heatable. It is also conceivable that a delivery device 9 used as a diaphragm pump is connected to a gas reservoir via the supply opening 18, in which case the gas (mixture) found in the gas reservoir is used as a driving medium. An embodiment is also conceivable in which an at least partially transparent syringe holder 2 is used instead of a syringe holder 2 provided with windows 21. Embodiments are also possible in which the syringe system 1 has a device to set or limit the pressure or negative pressure produced by the delivery device 9, in particular the injection rate and/or the removal rate caused thereby. The syringe system 1 can also have a display element for direct or indirect display of the pressure or negative pressure acting on the plunger 5 or the force acting on the plunger 5 and/or to display the charge status of the integrated power supply 10. The device for setting the pressure or negative pressure produced by the delivery device 9, as well as the display element can then be arranged on a readily visible location of the drive housing 8 that does not hamper operation or handling of the syringe system 1. The display device can then be supplied with current or power via the integrated power supply 10.

LIST OF REFERENCE NUMBERS

1 Pen-like syringe system
2 Syringe holder
3 Syringe
4 Syringe barrel
5 Plunger
6 Nozzle
7 Flange
8 Drive housing
9 Delivery device
10 Power supply
11 Receptacle
12 Cover
13 Drive channel
14 Connection piece
15 Vent channel
16 Button
17 Opening
18 Supply opening
19 Recess
20 Locking lever
21 Window
22 Restraining device
24 Joint
25 Sealing element
26 Flange receptacle
27 Locking lever joint
28 Passage
29 First input
30 Second input
31 Third input 32 Guide channel
33 Connection element
L Longitudinal direction

The invention claimed is:

1. A pen-like syringe system comprising:
a syringe holder for accommodating a syringe having a syringe barrel and a plunger movably guided in the syringe barrel;
a drive housing connected to the syringe holder;
an electric delivery device operated by an integrated power supply arranged in the drive housing for pneumatic operation of the plunger of the syringe inserted into the syringe holder with positive or negative pressure;
a drive channel connecting the electric delivery device to the plunger of the syringe inserted into the syringe holder; and
a button arranged on the syringe system for operation of the electric delivery device,
wherein the syringe system has a vent channel with a first end that is connected to the drive channel and a second end that is connected to the surroundings via an opening, the opening being closeable during activation of the button,
wherein the button is configured to be activated with a finger of a user and the delivery device is configured to be activated upon activating the button,
wherein the opening is configured, dimensioned, and arranged with respect to the button such that the opening is automatically closed by the finger when the button is activated, and
wherein the opening is opened towards the surroundings when the button is released, and the drive channel is configured to be vented to the surroundings and to stop subjecting the plunger of the syringe inserted into the syringe holder to positive or negative pressure upon releasing the button.

2. The system of claim 1, wherein the opening is located on the button.

3. The system of claim 1, wherein the opening is located proximal the button with a finger.

4. The system of claim 1, wherein the delivery device is a diaphragm pump and/or the plunger of the syringe inserted into the syringe holder is operated by air.

5. The system of claim 1, wherein the drive housing has at least one supply opening or a supply channel connected to the delivery device for connecting the delivery device to the surroundings or a gas reservoir.

6. The system of claim 1, wherein the syringe holder is hinged to the drive housing.

7. The system of claim 1, wherein the drive housing or the syringe holder has a lock lever for releasable fastening of the syringe holder to the drive housing or vice versa.

8. The system of claim 1, wherein the syringe holder is releasably connected to the drive housing via a bayonet lock or a thread.

9. The system of claim 1, wherein the syringe holder is at least partially transparent and/or has at least one laterally arranged window through which the syringe arranged in the syringe holder is at least partially visible.

10. The pen-like syringe system of claim 1, wherein the button is arranged on the syringe holder on or proximate a front end of the syringe holder facing away from the drive housing.

11. The system of claim 1, wherein the opening of the vent channel is arranged in the button or wherein the syringe holder has a recessed area in which the button and the opening of the vent channel are arranged, the opening of the vent channel pointing substantially in the longitudinal direction of the syringe system running through the drive housing and the syringe holder and activation of the button occurs perpendicular to the longitudinal direction.

12. The system of claim 1, wherein the syringe system is heatable in the area of the syringe holder.

13. The system of claim 1, wherein the syringe system is designed as a closed compact syringe system.

14. The system of claim 1, wherein the integrated power supply is a battery or an accumulator arranged in or on the drive housing.

15. The system of claim 14, further comprising a connection element for charging the integrated power supply.

16. The system of claim 1, wherein the syringe system has a device to set or limit the positive or negative pressure produced by the delivery device thereby limiting the injection rate and/or the removal rate of the syringe system.

17. The system of claim 1, further comprising a display element for direct or indirect display of the positive or negative pressure acting on the plunger or the force acting on the plunger and/or to display the charge status of the integrated power supply.

18. The system of claim 17, wherein the display element has an optical display that displays the power of the delivery device and/or the power tapped by the delivery device and/or the pressure or negative pressure acting on the plunger and/or the charge status of the integrated power supply.

19. The system of claim 1, further comprising a mechanical restraining device that prevents loosening of a cannula mounted on the syringe barrel of the syringe inserted into the syringe holder.

20. The system of claim 1, wherein the drive channel and/or the vent channel includes a tube connection or is designed as a tube connection.

21. The system of claim 1, wherein the syringe system is made of sterilizable materials that are stable during sterilization.

22. The system of claim 1, wherein the syringe system includes a syringe inserted into the syringe holder, the syringe having a syringe barrel and a plunger movably guided in the syringe barrel.

* * * * *